June 7, 1966 G. Y. ARAKAKI Plant Pat. 2,641
ALMOND TREE
Filed Aug. 31, 1964
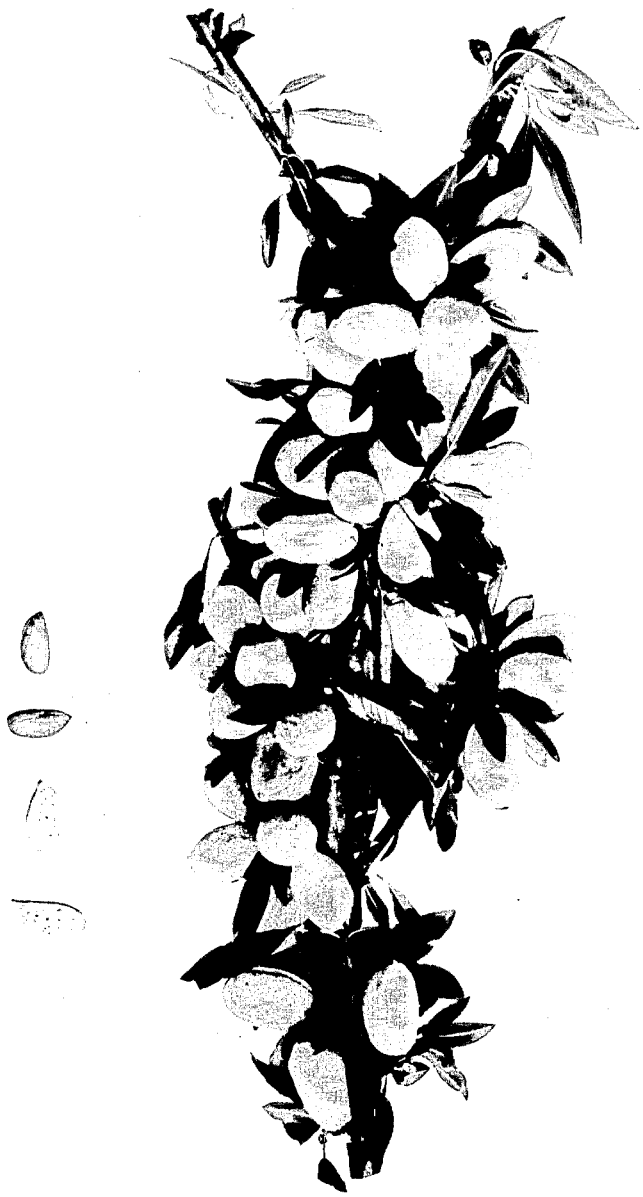
GENE Y. ARAKAKI
INVENTOR
Huebner & Worrel
ATTORNEYS United States Patent Office Plant Pat. 2,641
Patented June 7, 1966

2,641
ALMOND TREE

Gene Y. Arakaki, 3226 S. Athlone Road, Merced, Calif.

Filed Aug. 31, 1964, Ser. No. 393,465
1 Claim. (Cl. Plt.—30)

The present invention relates to a new and distinct variety of almond tree, and particularly to such a tree having certain characteristics similar to the unpatented Nonpareil but which matures later, while blooming at substantially the same time. While the crop production per tree of the instant variety is comparable to the production of a healthy tree of Nonpareil, it consistently produces a much heavier crop on a per acre basis. This is due to the instant variety's greater resistance to a disease known as almond bud failure which is frequently referred to as "crazy-top disease" with which the Nonpareil is generally susceptible and affected. Accordingly, the crop productivity per acre of the instant variety has been found to be approximately seven percent greater than the Nonpareil.

The subject almond tree originated from a Nonpareil bud propagated on a Lovell (unpatented) peach seedling and was discovered by the applicant as a sport in a row of such budded Nonpareil trees on Lovell peach seedlings growing in his nursery at 3226 South Athlone Road, Merced, California.

Subsequent to its origination and selection, applicant asexually reproduced the present variety of almond tree by budding on peach seedlings; such asexual reproduction having been accurate and true to the parent in all respects. The present variety is further characterized by its interfertility with the Nonpareil and Mission, unpatented, also known as the Texas. This interfertility is extremely desirable for a commercial variety of almond tree, since most of such varieties are incapable of self-pollination. Since the present variety blooms at the same time as the Nonpareil and has been employed with consistent success as its counterpart in interfertilization therewith, the commercial importance of the present variety is significant.

The present variety has certain characteristics similar to the unpatented Nonpareil, but is markedly different in its consistent bearing of regular crops, the size of its crops being much greater than the average crop of the Nonpareil under similar conditions. The blossoms of the subject variety, and the resulting fruit when pollinized, are arranged in clusters along the branches of the tree to a much greater degree than the Nonpareil, and the major portion of the crop is borne by the trees in this manner. The maturity date of the present variety is later than the Nonpareil, but earlier than the Mission variety.

The drawing is an illustration by photographic reproduction in color, of a portion of a branch of an almond tree of the new variety showing the partially mature crop arranged in clusters along the branch. The drawing also illustrates mature hulled nuts, both with and without the shell removed, which are representative of the crop borne by the new variety.

Referring now more specifically to the botanical details of this new and distinct variety of almond tree, the following is an outline description thereof in which color designations have been made comparison of fresh specimens to Maerz and Paul Dictionary of Color, Second Edition.

Tree generally: The new almond tree is of medium size and compares in form to the Nonpareil variety. It has been grown in the same orchard with Nonpareil and Mission varieties and consistently borne full crops each year during a test period of more than five years, whereas the Nonpareil and the Mission have borne alternately or less frequently.

Trunk: Medium caliper; surface typical for almonds.

Branches: Medium caliper.

Twigs during growing season: Larger bud than Nonpareil, but shorter bud stem; heavier and darker calyx scale at base of bud. Buds more numerous than Nonpareil, closely spaced and having a marked tendency to be arranged in clusters along the branches. New growth more reddish in color than Nonpareil.

Leaves: Lengths 5 to 7½ cm.; width 1 to 2 cm.; less sharply creased than Nonpareil and presents a flattened appearance; acuminate to lanceolate, medium thickness; glossy; smooth.

*Color.*—Slightly lighter green than Nonpareil. Upper surface: Bright, glossy, Plate 21–I–8. Lower surface: Plate 21–G–3.

*Margin.*—Minutely serrated, finer serrations than Nonpareil.

*Petiole.*—Medium.

*Glands.*—Infrequent and usually paired in laterally opposed relation.

Blossoms: Arranged in clusters to a much greater degree than Nonpareil; major portion are groups of clusters of three or more.

*Color.*—White to very light pink Plate 1–B–1 to A–2.

*Blooming period.*—Substantially concurrent with Nonpareil.

Fruit: Matures usually during the second week in September which is approximately three weeks later than Nonpareil but about one week prior to unpatented Texas or Mission variety. High quality and consistently regular in bearing, as distinguished from Nonpareil which normally alternates between heavy and light bearing in successive years. Higher quantity borne by trees of new variety as compared to Nonpareil trees of same age and both grown in applicant's orchard. No tests yet conducted outside of San Joaquin Valley of California.

*Hull.*—Similar in color and general appearance to Nonpareil.

*Shell size and form.*—Small and thick, between Nonpareil and unpatented Neplus. Medium to pronounced wing on ventral side. Dorsal side longitudinally arcuate. Small stem scar. Small pointed apex. Color of shell is light, Plate 10–D–2.

*Kernel.*—Usually single kernel in each shell; very few doubles as distinguished from Nonpareil; well filled; shells out at sixty percent meat; average, twenty-four kernels per ounce. Pellicle: Thin and minutely veined. Relatively smooth. Lighter color than Nonpareil, approximately Plate 12–H–9 to 12–K–11. Meat: White; very good quality and flavor.

It is expected that the described characteristics of the subject variety of almond may vary in slight detail when grown under different soil and climatic conditions but the distinctive features have proved constant in the reproduced variety under the conditions existing in the San Joaquin Valley of California.

Having thus described and illustrated my new variety of almond tree, what is claimed as new and desired to be secured by Letters Patent is:

A new and distinct variety of almond tree substantially as described and illustrated characterized particularly as to novelty by its blooming period being substantially concurrent with the Nonpareil, by its general similarity to the Nonpareil in tree appearance and growing habits, by its maturing period being later than the Nonpareil but prior to the Mission variety, by its consistent bearing of crops heavier than the Nonpareil, and by its tendency to bear its crop in clusters along its branches.

No references cited.

ANTONIO F. GUIDA, *Primary Examiner.*

ABRAHAM G. STONE, *Examiner.*

R. E. BAGWILL, *Assistant Examiner.*